US008953153B2

(12) United States Patent
Wall (10) Patent No.: US 8,953,153 B2
(45) Date of Patent: Feb. 10, 2015

(54) SYSTEM AND METHOD FOR POST-TENSIONED TENDON MONITORING

(71) Applicant: Electric Power Research Institute, Inc., Palo Alto, CA (US)

(72) Inventor: James Wall, Charlotte, NC (US)

(73) Assignee: Electric Power Research Institute, Inc., Palo Alto, CA (US)

( * ) Notice: Subject to any disclaimer, the term of this patent is extended or adjusted under 35 U.S.C. 154(b) by 210 days.

(21) Appl. No.: 13/852,345

(22) Filed: Mar. 28, 2013

(65) Prior Publication Data

US 2013/0335727 A1    Dec. 19, 2013

Related U.S. Application Data

(60) Provisional application No. 61/660,204, filed on Jun. 15, 2012.

(51) Int. Cl.
| | |
|---|---|
| *G01B 11/16* | (2006.01) |
| *G01L 1/24* | (2006.01) |
| *G01M 5/00* | (2006.01) |
| *G01N 3/08* | (2006.01) |
| *G01L 5/00* | (2006.01) |
| *G01L 5/10* | (2006.01) |
| *G21C 17/10* | (2006.01) |

(52) U.S. Cl.
CPC ............... *G01L 1/24* (2013.01); *G01M 5/0025* (2013.01); *G01M 5/0041* (2013.01); *G01N 3/08* (2013.01); *G01L 5/0033* (2013.01); *G01L 5/105* (2013.01); *G21C 17/10* (2013.01)
USPC .............................................. 356/32; 356/34

(58) Field of Classification Search
USPC .......................................... 356/32–35.5, 429
See application file for complete search history.

(56) References Cited

U.S. PATENT DOCUMENTS

| | | | | |
|---|---|---|---|---|
| 5,138,879 A | * | 8/1992 | Shofner et al. | 73/160 |
| 5,633,467 A | * | 5/1997 | Paulson | 73/800 |

OTHER PUBLICATIONS

Case Study-Nuclear Power. "Robert E. Ginna Nuclear Generating Station Pilot Project, Assessing the Condition of Concrete Containment Structures", Jan. 2012.
"Post-Tensioned Tendon Monitoring on the Robert E. Ginna Nuclear Containment Structure", Atlanta, GA, PRWEB, Apr. 30, 2012.
Bruck, "Long Term Operation: Concrete and Containment for LTO, Comprehensive Containment Examination for LTO", Aug. 16, 2011.

\* cited by examiner

*Primary Examiner* — Tri T Ton
(74) *Attorney, Agent, or Firm* — Curatolo Sidoti Co., LPA; Joseph G. Curatolo; Salvatore A. Sidoti (57) ABSTRACT

A system and method for post-tensioned tendon monitoring includes at least one optical sensor arranged in monitoring proximity to a post-tensioned tendon, a test instrument in communication with the optical sensor, a processor capable of managing operation of the test instrument, a storage device and a display. They further include a database adapted to contain sensor baseline information and sensor measurement data. The test instrument is capable of sending a first wavelength to the optical sensor and receiving a second wavelength from the optical sensor, wherein at least one of the instrument or the processor is configured to analyze the second wavelength and output sensor measurement data for storage in the database. The processor is configured to calculate an amount of tensile loading which exists in the post-tensioned tendon, based on the sensor measurement data and the sensor baseline data, and to provide an output.

18 Claims, 5 Drawing Sheets

SYSTEM AND METHOD FOR POST-TENSIONED TENDON MONITORING

This Application claims the benefit of the filing date under 35 U.S.C. §119(e) of U.S. Provisional Application for Patent Ser. No. 61/660,204, filed Jun. 15, 2012, which is incorporated herein by reference.

Commercial nuclear power plants in the United States include structures whose performance and function are necessary for the protection and safety of plant operating personnel and the general public, as well as the environment. Nuclear power plant designs feature reliable and diverse safety systems and strong physical barriers to prevent incidents that could pose a threat to public health and safety in the event of a release of material from reactor vessel. The same features that safeguard the public and the environment from such a release also protect the reactor vessel from outside disturbances.

A pressurized-water reactor (PWR) containment structure is typically protected by structure with typically greater than about 3 foot thick steel-reinforced concrete walls with a steel liner. The reactor vessel itself is made of steel roughly 6-8 inches thick. A PWR containment structure generally comprises a concrete foundation, vertical cylindrical walls, and a dome. These steel-reinforced concrete containment structures are designed to withstand the impact of many natural disasters, including hurricanes, tornadoes, earthquakes and floods, as well as airborne objects with a substantial force.

A state-of-the-art computer modeling study has confirmed that the primary structures of a nuclear plant would withstand the impact of a wide-bodied commercial airliner. The study concluded that typical nuclear plant containment structures, as well as used fuel storage pools, and steel and concrete fuel storage containers, would withstand the impact forces and shield the fuel.

The PWR containment structures in the United States are predominantly large, unbonded post-tensioned concrete designs. Post-tensioning is a method of reinforcing (strengthening) concrete or other materials with high-strength steel strands or bars, typically referred to as tendons. During construction, concrete is cast around a plastic, steel or aluminum duct and a set of tendons are fished through the duct. Once the concrete has hardened, the tendons are tensioned by hydraulic jacks that react against the concrete member itself. When the tendons have stretched sufficiently, according to the design specifications, they are wedged in position and maintain tension after the jacks are removed, transferring pressure to the concrete. The compression that results from the post-tensioning counteracts the tensile forces created by subsequent applied loading, significantly increasing the load-carrying capacity of the concrete.

In the United States, the Atomic Energy Act and regulations of the United States Nuclear Regulatory Commission limit commercial power reactor licenses to an initial 40-year period, but also permit such licenses to be renewed. This 40-year term for reactor licenses was based on economic and antitrust considerations—not on limitations of nuclear technology. Due to this selected period, however, some structures and components may have been engineered on the basis of an expected 40-year service life. Currently the United States has over 100 nuclear power plant units licensed for commercial operation that provide about 20% of the electricity supply. Older plants have surpassed their initial operating license periods and have entered the period of license extension.

Exposure to the environment (e.g., temperature, moisture, cyclic loadings, etc.) can produce degradation of reinforced concrete structures. Post-tensioning systems are susceptible to degradation which can occur as a result of corrosion, elevated temperatures, and loss of pre-stressing force due to tendon relaxation and concrete creep and shrinkage. Traditionally, tendon tension has been verified with a periodic "lift-off" procedure, however, this procedure is costly, time consuming, and only provides insight during the tests.

In order to ensure the safe operation of nuclear power plants, it is essential that the effects of age-related degradation of nuclear power plant structures be assessed. What is needed are improved monitoring systems and methods to help maintain an acceptable level of reliability for post-tensioned structures over their service life and to support long-term operation of existing nuclear plants.

Embodiments of the subject matter are disclosed with reference to the accompanying drawings and are for illustrative purposes only. The subject matter is not limited in its application to the details of construction or the arrangement of the components illustrated in the drawings. Like reference numerals are used to indicate like components, unless otherwise indicated.

Provided is a system and method for post-tensioned tendon monitoring. According to certain illustrative embodiments, a system for post-tensioned tendon monitoring comprises (a) at least one optical sensor arranged in monitoring proximity to a post-tensioned tendon, (b) a test instrument in communication with the at least one optical sensor, (c) a processor capable of managing operation of the test instrument, (d) a storage device associated with the processor, (e) a display in communication with the processor, (f) a database stored on the storage device adapted to contain sensor baseline information and sensor measurement data, wherein the test instrument is capable of (i) sending a first wavelength to the at least one optical sensor and (ii) receiving a second wavelength from the at least one optical sensor, wherein at least one of the instrument or the processor is configured to analyze the second wavelength and output sensor measurement data for storage in the database, and the processor is adapted to access the database and configured to calculate an amount of tensile loading which exists in the post-tensioned tendon, based on the sensor measurement data and the sensor baseline data, and to provide an output to the display indicative of a feature of the tensile loading which exists in the post-tensioned tendon.

According to other illustrative embodiments, a computer-implemented method for post-tensioned tendon monitoring comprises (a) determining an expected value of post-tensioned tendon tensile loading, (b) receiving a signal from at least one optical sensor associated with a post-tensioned tendon assembly, (c) analyzing the signal to determine a measured value of the post-tensioned tendon tensile loading, (d) optionally comparing the measured value with the expected value and (e) generating a data output.

Figure 1:
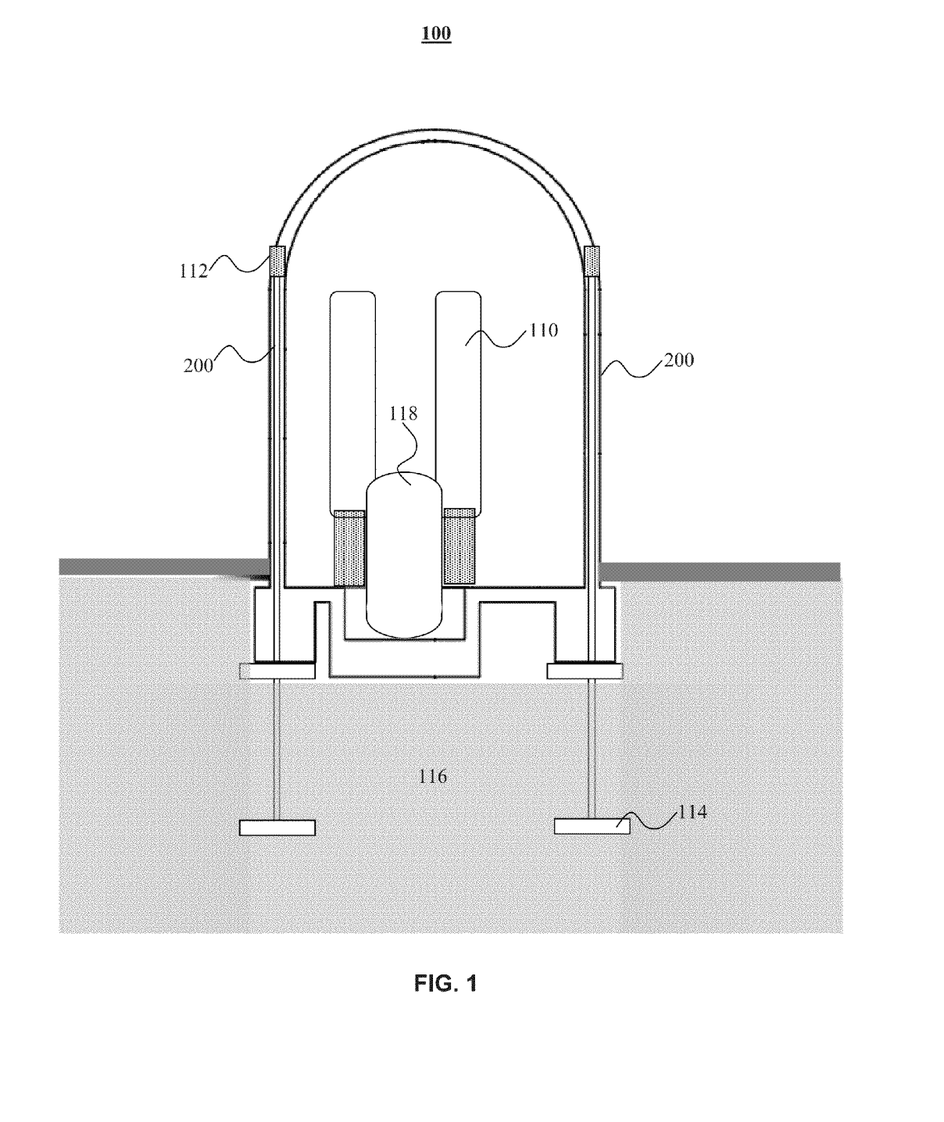
FIG. 1 a graphical representation of an illustrative post-tensioned nuclear containment structure.

As shown in FIG. 1, an illustrative pressurized water reactor containment structure 100 may employ a series of post-tensioned steel cable tendons 200 installed vertically through the containment concrete in conduits. An exemplary pressurized water reactor containment structure 100 may include more than one-hundred-fifty post-tensioned tendons 200. The containment structure 100 encloses the reactor's steam generators 110 and pressurizer 118, and is designed, in an emergency, to contain the escape of material from the reactor vessel and to provide protection from outside forces. The post-tensioned tendons 200 may each be composed, for example, of 90 wires and are anchored at both ends 112, 114. The post-tensioned tendon may be anchored at the base 114 in bedrock or sandstone 116, and at the top by an adjustable anchor 112. The post-tensioned tendons 200 supply a tension force to the concrete, giving it greater strength to withstand an increase in pressure from a potential breach of the primary containment system and to resist the effects of outside elements.

For the purposes of this disclosure, a post-tensioning "tendon" is defined as a complete assembly comprising the anchorages, the pre-stressing steel wires, strands or bar, the sheathing or duct, and any corrosion-inhibiting coating, such as grease, surrounding the pre-stressing steel. There are two main types of post-tensioning: unbonded and bonded (grouted). An unbonded tendon is one in which the pre-stressing steel is not bonded to the concrete that surrounds it except at the anchorages. The post-tensioned tendons of the present disclosure refer generally to unbonded tendons.

In a post-tensioned concrete structure, the axial force in a stressed tendon is transferred to the concrete primarily by the anchors provided at each end. Tensioning of the tendons is generally accomplished by using a large hydraulic rotary device to drive an adjustable anchor in tension. After the tendons have been tensioned, a set of steel clamshell shims may be used to keep the anchor in tension. Since the force of a tendon is resisted by the anchors at each end, the long-term integrity of the tendons and anchors throughout the service life of the structure are of concern.

According to regulatory requirements, periodic lift-off tests are mandatory for nuclear power plants having unbonded, post-tensioned containments. The purpose of a lift-off test is to verify the force of a tendon after it has been stressed. This method of determining tendon load can be dangerous and is fairly complicated and expensive. A calibrated hydraulic rotary device is affixed to the tendon button head anchor and pulled to measure the effective force in the tendon. If the force required to lift the tendon head plate is lower than a predetermined level, tension adjustments may be made at the top anchor, using additional shims. The need for specialized heavy lifting equipment and access issues make this test expensive and potentially problematic. Further, periodic testing provides only limited information on tendon condition and is not suited to ongoing or real-time monitoring of tendon tension.

Regulations may require, for example, lift-off testing of fourteen randomly selected tendons every five years for a nuclear containment dome structure with 160 total tendons. The tendons may each be composed of 90 wires. Acceptance criteria is based on the lift-off load values indicating less than thirty-eight wire breaks across the fourteen tendons under test. The test criteria provides greater than 95% confidence that the number of broken wires in the remaining tendons is acceptable. However, this form of testing provides only limited information on tendon condition.

Traditionally, tendon tension has been verified with periodic "lift-off" procedures, however, continuous monitoring with optical sensors can reduce costs and may provide real-time assurance of containment dome integrity.

Figure 2:
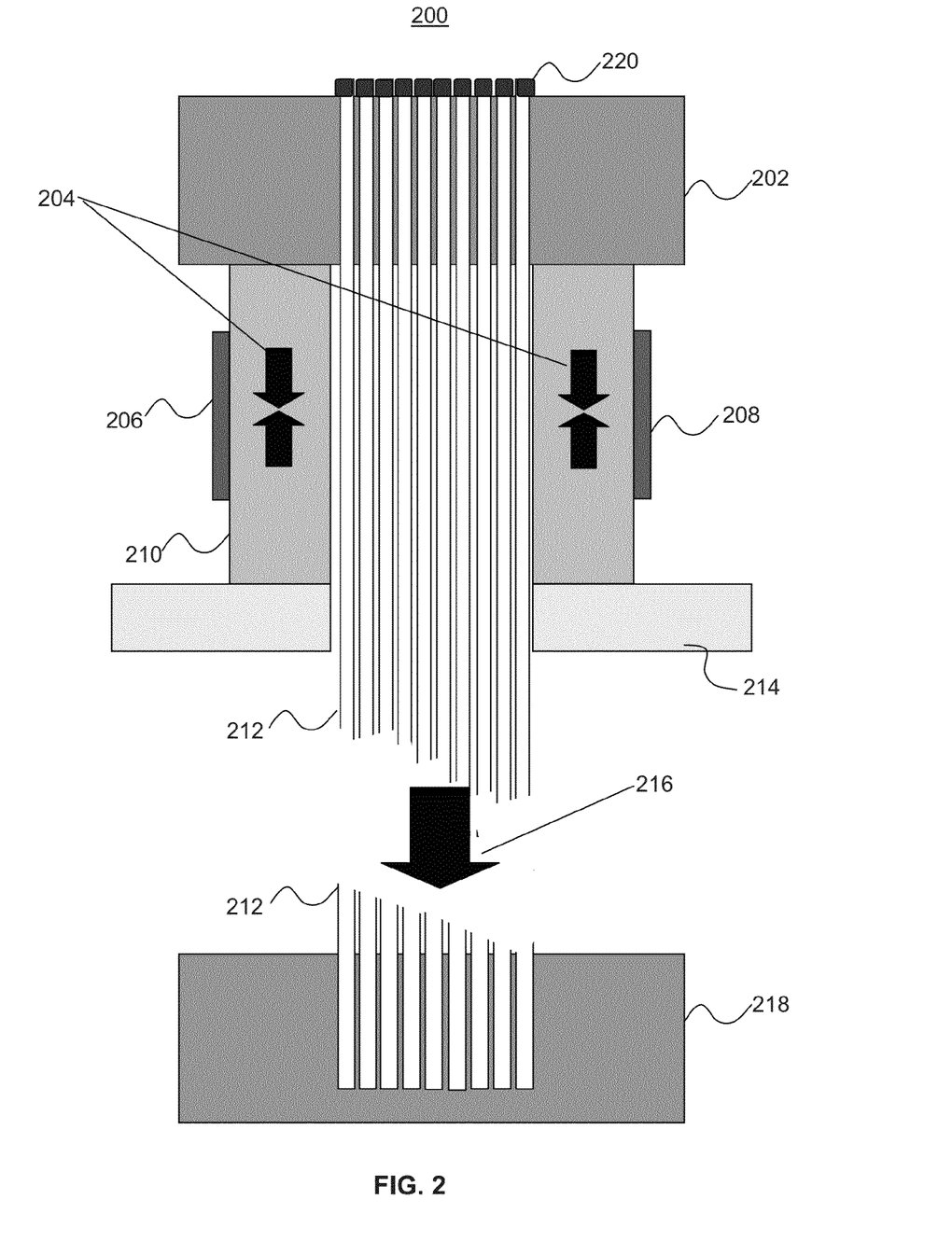
FIG. 2 is a graphical representation of an illustrative post-tensioned tendon assembly.

Referring to FIG. 2, a post-tensioned tendon 200 comprises tendon wires 212, an anchor plate 202, a baseplate 214, shim 210 and an anchor 218. In certain embodiments the tendon wires 212 include a cold-forged "button-head" 220, having a diameter of approximately ⅜ inch, at each end. The button-head wire tendons 212, 220 are passed through an anchor plate 202 and the anchor plate 202 is pulled using, for example, a hydraulic jack, thereby imposing a tensile load 216 on the tendon 200. A shim 210 is inserted between the baseplate 214 and the anchor plate 202 to maintain tension in the wire tendons 212. The shim 210 may comprise a two-part clamshell structure. The wire tendons 212 are anchored at the opposite end by anchor 218 which may be embedded in, for example, bedrock or sandstone. In other embodiments, the tendon wires may be anchored on each end by a button-head style anchor. The tensioned tendon wires exert compressive forces 204 on the clamshell shims.

Still referring to FIG. 2, sensor arrays 206, 208 may be located within monitoring proximity of the wire tendons 212. In accordance with an embodiment, the sensors 206, 208 may be engaged with or affixed to the clamshell shim of the post-tensioned tendon assembly 200. The optical sensor arrays 206, 208 are operative to provide a signal representative of the compressive forces 204 exerted on the shim 210.

In an embodiment, when engaged with the clam shell shim 210 of a post-tensioned tendon, the strain gage sensor unstrained state will be under tendon load. Therefore, the strain signal may be biased commensurate with the tendon load. The compression force 204, or biased strain, in the shim 210 may be measured utilizing a hydraulic rotary device (i.e. lift-off procedure) to measure the tendon load 216 in the instrumented tendon. The biased strain in the shim 204 may be converted to load in the shim using, for example, Hooke's law.

Hooke's law of elasticity is an approximation which asserts that the displacement or size of a deformation is directly proportional to the deforming force or load. Mathematically, Hooke's law states that $F=-kx$, where x is the displacement of, for example, a spring's end from its equilibrium position; F is the restoring force exerted by the spring on that end; and k is a constant called the rate or spring constant. Stress is the force on unit areas within a material that develops as a result of an externally applied force. Strain is the relative deformation produced by stress. In some circumstances, stress may be proportional to strain.

By force balance, the strain in the shim 204 is proportional to the load in the tendon 212. The strain in the shim may be converted to tendon load and may be sampled in real time to provide tendon force or tendon tensile load data. Data may be recorded continuously for each instrumented tendon and evaluated for conformance with design loads and/or for comparison to expected post-tensioned tendon tensile loading values.

Figure 3:
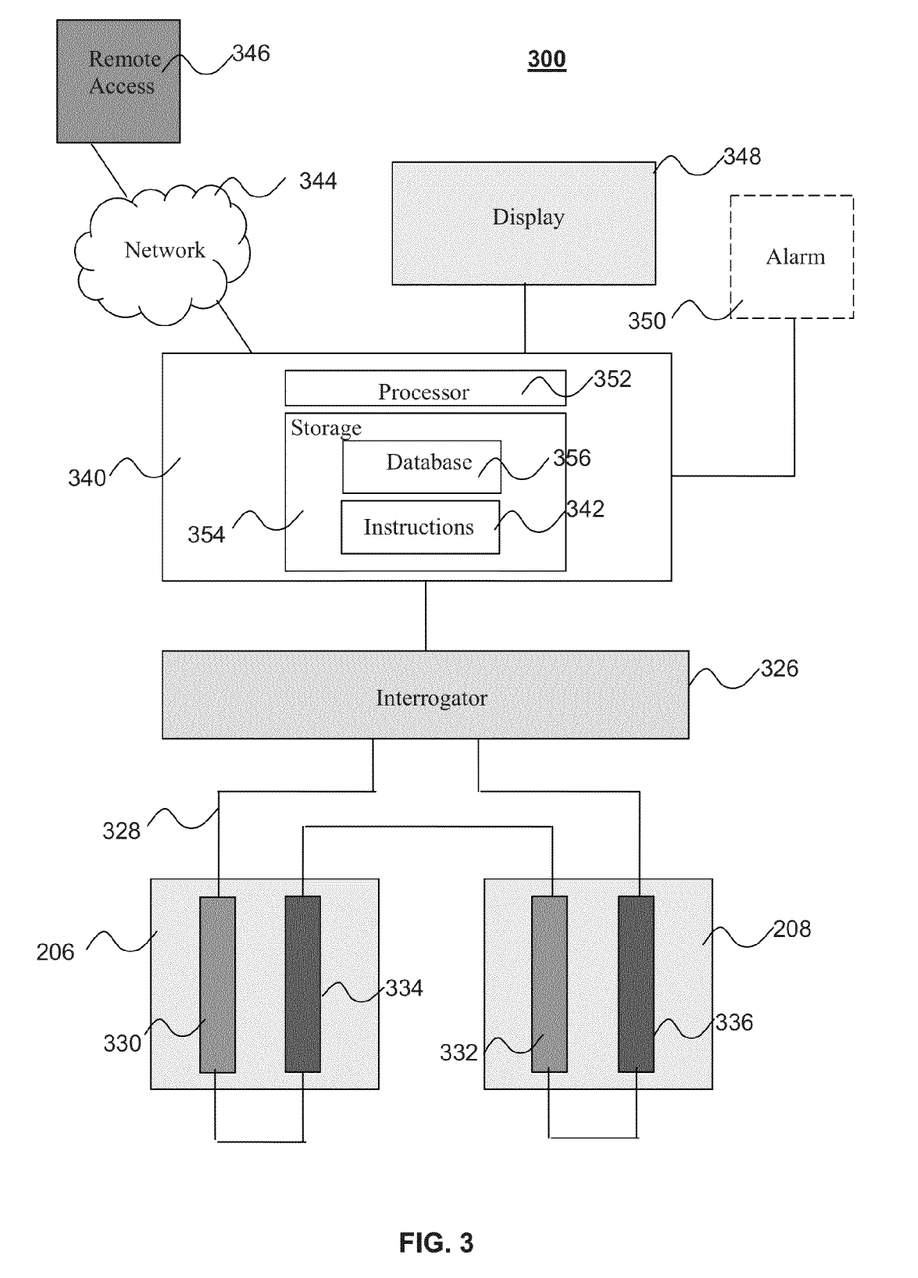
FIG. 3 is a block diagram of an illustrative post-tensioned tendon monitoring system.

As shown in FIG. 3, the sensor arrays 206, 208 may comprise optical strain gage sensors 330, 332 and optical temperature sensors 334, 336. The sensors may be connected to each other in series utilizing, for example, fiber optic cable 328. A monitoring system 300 in accordance with the present disclosure may comprise, for example, a plurality of sensors such that all, or a portion, of the post-tensioned tendons of a concrete structure may each be monitored.

In accordance with an embodiment, an optical temperature compensation gage 334, 336 may be utilized to provide temperature compensation data for the optical strain gage measurements. Temperature induced wavelength changes may be subtracted from those induced by both temperature and strain, yielding a pure strain measurement. Measurement of relative temperature for compensation of strain measurements may be accomplished by the use of a suitable, commercially available optical temperature gage sensor.

In an illustrative embodiment, the software and hardware of the present system and method may provide features such as acquisition, computation, analysis and visualization of optical sensor data. The software and hardware may be capable of converting optical sensor data to engineering units and displaying the results in real-time.

In an embodiment, baseline sensor data may be determined for each instrumented post-tensioned tendon by, for example, performance of a lift-off test. The lift-off test measurement value may be stored in the database 356 as baseline data for the appropriate sensor. An amount of tensile loading in the instrumented tendon may subsequently be calculated utilizing sensor measurement data for comparison with the baseline data.

The optical sensors that are useful in the present system and method are those known in the art which are capable of providing a signal representative of temperature, or strain associated with an object. With respect to post-tensioned tendon assemblies, conventional fiber optic sensors which report a signal to an optical interrogator 326 via a fiber optic cable 328 may be used.

Fundamentally, a fiber-optic sensor works by modulating one or more properties of a propagating light wave, including intensity, phase, polarization, and and/or frequency, in response to the environmental parameter being measured. A fiber Bragg grating (FBG) optical sensor reflects a wavelength of light that shifts in response to variations in temperature and/or strain. FBG sensors may be constructed by using holographic interference or a phase mask to expose a short length of photosensitive fiber to a periodic distribution of light intensity. The refractive index of the fiber is permanently altered according to the intensity of light that it is exposed to. The resulting periodic variation in the refractive index is called a fiber Bragg grating.

When a light beam is sent to an FBG sensor, reflections from each segment of alternating refractive index interfere constructively only for a specific wavelength of light, called the Bragg wavelength. This effectively causes the FBG to reflect a specific frequency of light while transmitting all others. Because the Bragg wavelength is a function of the spacing between the gratings, FBG sensors can be manufactured with various Bragg wavelengths, which enables different FBG sensors to reflect unique wavelengths of light.

In certain embodiments, FBG sensors 330, 332, 334, 336 may be located in monitoring proximity to a post-tensioned tendon assembly 200. The strain or temperature of the respective FBG sensor is encoded in the Bragg wavelength which may be measured using an instrument, for example, an optical interrogator 326. A commercially available optical interrogator, for example, the Micron Optics sm225Optical Sensing Interrogator may be utilized.

The instrumented sensor may include a sensor array 206, 208 comprising two FBG strain gages 330, 332 and two optical temperature sensing gages 334, 336 connected in series. Sensor arrays 206, 208 comprise an illustrative sensor array in accordance with the present system and method. The sensor array 206, 208 may be arranged within monitoring proximity of the post-tensioned tendon 200. In accordance with an embodiment, the sensor array is engaged with the anchor shim 210 of the post-tensioned tendon assembly 200.

In an embodiment, a tendon anchor may be exposed by removing the grease cap and grease surrounding the tendon assembly anchorage. After the grease has been removed, one fiber optic strain gage and one fiber optic temperature sensor may be affixed to each half of a clamshell shim 210. The gages may be oriented in the vertical (loading) direction and fixed by spot welding directly on the shim, or may be fastened by other means, for example, utilizing a suitable adhesive. The two strain gage arrays, one attached to each half of the clamshell shim, may then be run in series to an instrument, for example, an optical interrogator 326 or a fiber optic signal generator and spectrum analyzer. The analyzed signal may provide data representative of the strain in the clamshell shims for the instrumented tendon. In accordance with an embodiment, a tendon may be monitored utilizing a sensor array comprising at least two optical strain gages and at least two optical temperature gages connected in series. In some embodiments, a plurality of post-tensioned tendons, associated with a concrete structure, may be monitored utilizing, for example, a plurality of sensor arrays. The plurality of sensor arrays may be connected in parallel to each other.

The FBG sensors 330, 332, 334, 336 may be connected to an optical interrogator 326 via a fiber optic cable 328. Light may be sent into the fiber from the instrument 326 and reflected back to the instrument 3262 from the FBG sensors 330, 332, 334, 336. The reflected light travels back to the interrogator's 326 photo detectors and may be compared to wavelength references to determine the position of the center wavelength of the FBG sensor.

In an illustrative embodiment, the optical interrogator light source may be a tunable laser which concentrates energy in a narrow band. The instrument may operate by sweeping a very narrow band of light across a wavelength range while synchronously using a photodetector to measure the reflections from the FBG sensors. When the wavelength of the tunable laser matches the Bragg wavelength of the FBG sensor, the photodetector sees a corresponding response. The wavelength at which this response occurs corresponds to the temperature and/or strain of the FBG sensor.

When more than one FBG sensor is present on a fiber, the instrument may use wavelength division multiplexing (WDM) to discriminate between one FBG and the next. WDM FBG sensors may be at distinctly different nominal center wavelengths from their neighbors, and the interrogator may utilize the unique FBG wavelengths to keep track of which sensor is which. Sensor capacity on each fiber may be determined by the range that each sensor will measure and the total spectral range of the instrument. WDM ranges may be very large and may accommodate multiple sensors per fiber.

In further embodiments, an interrogator 326 may be connected to a secure server 340. The server 340 may include a processor 352, a storage device 354, a display 348 and other components typically present in a computer. The storage device 354 may comprise memory for storage of one or more databases 356 and for storage of information accessible by the processor 352, including instructions 342 that may be executed by the processor 352 and data, that may be retrieved, manipulated or stored by the processor 352. The server 340 runs software applications and may interface with one or more interrogator modules 326. The software applications may interface with the interrogator and server hardware to collect, analyze, present and store sensor measurement data. The sensor measurement data representative of post-tensioned tendon tensile loading, may be acquired in real-time for visualization in real-time.

In other embodiments, the interrogator 326 and the server 340 may be integrated and may provide data acquisition, sensor calibration, data visualization, and/or data storage capabilities. The interrogator 326 may scan an optical wavelength range to identify all connected FBG sensors 330, 332, 334, 336. The interrogator 326 may parse scans into individual sensor measurements and scale the data in appropriate engineering units. For example, sensor wavelength information may be converted to engineering units, for example, 1.2 picometers of wavelength shift may correspond to 1 microstrain. In certain embodiments, the sensor measurement data may be exported for use in other software applications. In some embodiments, the present system and method may be configured for storage and retrieval of acquired tensile load measurements for historical analysis.

In further embodiments, the post-tensioned tendon monitoring system may be accessed remotely 346 via a network 344. The monitoring system may provide an output, for example, via a display 348, printout, or other means. In an embodiment, output may be made available in real-time, for real-time monitoring, or may be stored and made available for later use. In an aspect of the present disclosure, the system may generate an alarm 350, for example, when the measured tendon tensile load value is not within tolerance of a predetermined value. An alarm, or alert, may comprise at least one, or any combination, of an audible indicator, visual indicator, sensory alert, flashing light, phone call, tweet, email, pager notification, text message, instant message, social media message or the like.

In certain embodiments, the present system and method may be configured as a long-term monitoring system that records acquired tensile load measurements in real-time for detection of possible anomalies and immediate activation of an alert and/or an alarm.

Figure 4:
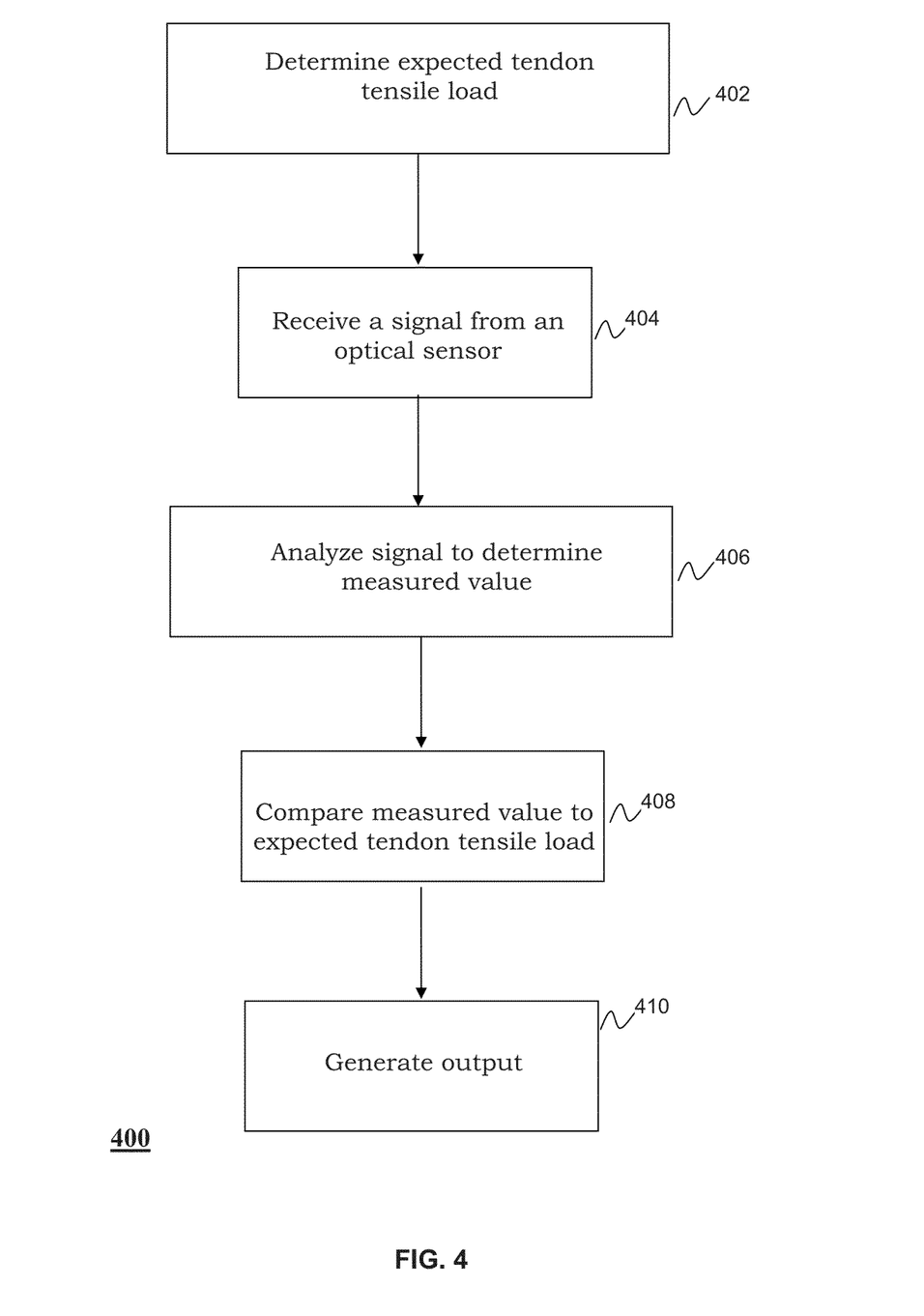
FIG. 4 is a flow diagram in accordance with an illustrative embodiment of the disclosed system and method.

Turning to FIG. 4, an illustrative method for post-tensioned tendon monitoring 400 begins by determining, that is, providing an expected or design tendon tensile load 402. In accordance with standard industry procedures, details for post-tensioned members are first developed by the design engineer or architect. Structural drawings for post-tensioned structures typically provide the post-tensioning requirements in terms of final effective forces, for example, in units of force or "kips". One kip is equal to 1,000 lb.-force.

Receiving a signal from an optical sensor 404 may comprise, for example, receiving optical strain gage sensor data representative of strain forces in an anchor portion of a post-tensioned tendon assembly. Such data may be the result of analysis of a wavelength of light returned by the sensor to an interrogator, optionally by a processor associated with or in communication with the interrogator. In further embodiments, a signal from an optical sensor may include temperature data representative of temperature data associated with the monitored tendon and the optical strain gage sensors.

The optical sensor data may be analyzed 406, for example, to determine a measured amount of tensile loading which exists within a post-tensioned tendon based on the anchor strain force data. The anchor force strain data may be compensated by optical temperature sensor data, thus compensating the measured value of the post-tensioned tendon tensile loading with the strain due to temperature.

In certain embodiments, the method may include the optional step of comparing the measured value of the post-tensioned tendon loading to an expected or design tendon tensile load 408. In other embodiments, sensor data may be stored or output directly without comparison to an expected tendon tensile load.

An output may be generated 410. The output may comprise a visualization, or graphical representation, of measured post-tensioned tendon tensile loading values or any other form capable of communicating the information of interest. The output may comprise a quantitative indicator, or a threshold output such as high/medium/low. Examples of such output include spreadsheets, charts, plots, graphs, or any other representation to identify information of interest. For instance, the output may be presented on a user's display utilizing images, colors, fonts, etc. In certain embodiments, visualization of post-tensioned tendon tensile loading data may be displayed, or otherwise provided, in real-time. In other embodiments, the present system and method may be configured for storage and retrieval of acquired tensile load measurements for historical analysis.

In further embodiments, a tolerance may be established for the expected value of post-tensioned tendon tensile loading. A comparison of the expected or design post-tensioned tendon tensile loading value with the sensor data, or measured value, may be performed. If the measured value is not within the established tolerance of the expected value, an alarm may be generated. An anomalous tendon tensile load value may be identified and an output 410, for example, an alert, alarm or notification may be generated and output automatically. An anomalous tendon tensile load may comprise, for example, a tensile load that is not within the established tolerance of the expected value.

Figure 5:
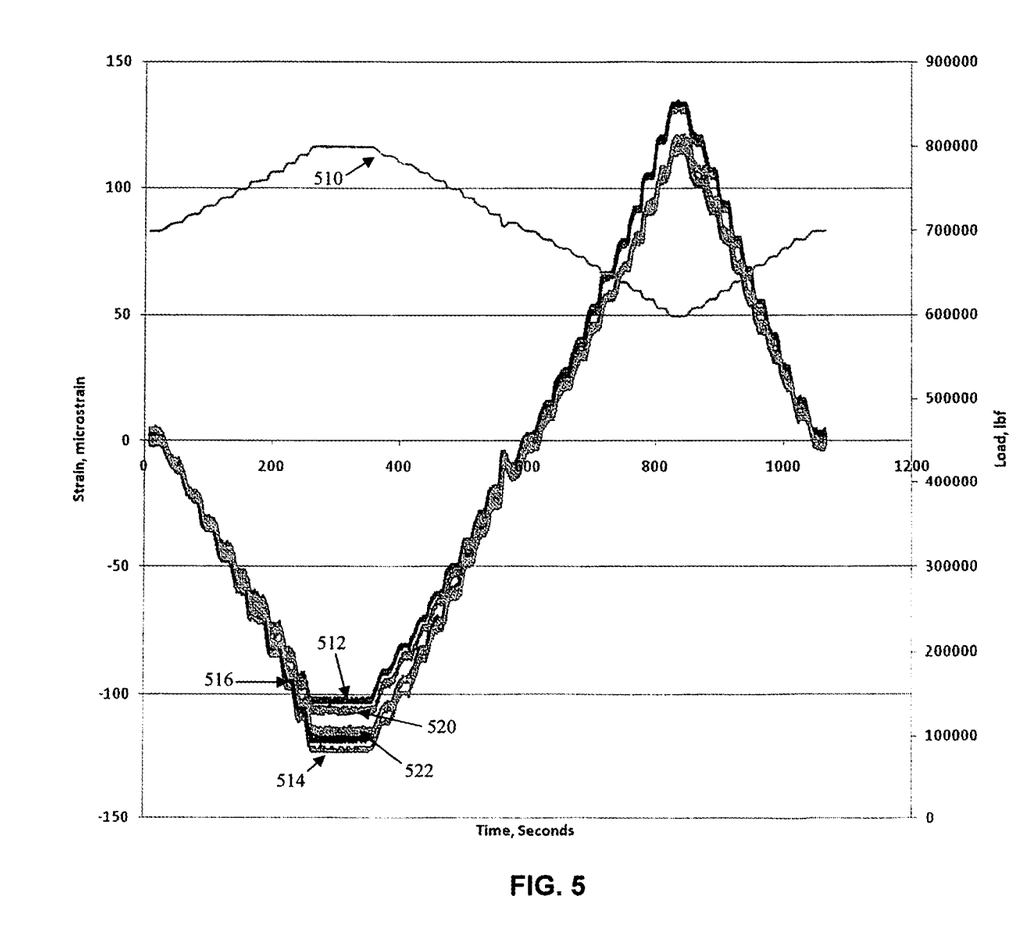
FIG. 5 is a graphical representation of illustrative output of the subject system and method, in accordance with an illustrative embodiment.

The post-tensioned tendon monitoring system and method have been tested utilizing a 5,000,000 pound load frame. A prototypical tendon anchor shim was fabricated and optical gages applied to the shim under a 700,000 lb load. Foil strain gages were utilized in addition to the optical strain gages, as a comparison. FIG. 5 is a graphical representation of the measured output of the FBG optical strain gages 520, 522 as compared to the foil gages 512, 514, 516. The load 510 was cycled in 1,000 lb steps from 690,00 to 710,000 lb and in 10,000 lb step from 0 to 700,000 lb. Data was recorded from both the foil gages 512, 514, 516 and the optical gages 520, 522. The test data reveals that the fiber optic strain gage measurements agree with the average of the foil gage measurements. Further, the fiber optic strain gages provided more consistent results, with respect to each other, than the foil gages.

A containment tendon shim may hold, for example, a tendon comprised of 90 wires. Under a typical 700,000 lb. load, a broken wire would result in a change in the load of approximately 7.8 kips. Utilizing a 95% confidence level, the sensitivity of the test system was calculated from the test data and yielded a detectable change in load of ±2 kips (1 kip=1,000 lb.-force).

Therefore, the FBG strain gages exceeded the resolution required to detect a ~0.1% change in tensile load, i.e., the FBG strain gages were shown to be operative to capture the shift in load on a shim due to the loss of one wire in a 90 wire tendon under a 700,000 lb load. Based on the test data, it is evident that FBG strain gages may be used to monitor post-tensioned tendons.

It will be understood that the embodiments described herein are merely exemplary, and that one skilled in the art may make variations and modifications without departing from the spirit and scope of the invention. The embodiments described above are not necessarily in the alternative, as various embodiments may be combined to provide the desired results.

The invention claimed is:

1. A system for post-tensioned tendon monitoring comprising:
    at least one optical sensor, which comprises a sensor array, arranged in monitoring proximity to a post-tensioned tendon;
    wherein said sensor array comprises:
        a first optical strain gage engaged with a first optical temperature sensor;
        a second optical strain gage engaged with a second optical temperature sensor, wherein the gages are connected serially; and wherein data associated with the first and second optical strain gages is capable of being compensated by data associated with the first and second temperature sensors;

a test instrument in communication with the at least one optical sensor;

a processor capable of managing operation of:
the test instrument,
a storage device associated with the processor, and
a display in communication with the processor;

a database stored on the storage device, wherein the database is adapted to contain sensor baseline information and sensor measurement data;

wherein the test instrument is capable of sending a first wavelength to the at least one optical sensor and receiving a second wavelength from the at least one optical sensor, wherein at least one of the instrument or the processor is configured to analyze the second wavelength and output sensor measurement data for storage in the database; and wherein the processor is adapted to access the database and configured to calculate an amount of tensile loading which exists in the post-tensioned tendon, based on the sensor measurement data and the sensor baseline data, and to provide an output to the display indicative of a feature of the tensile loading which exists in the post-tensioned tendon.

2. The system of claim 1, wherein the post-tensioned tendon is installed within a concrete structure.

3. The system of claim 2, wherein the concrete structure is a nuclear containment structure.

4. The system of claim 1, wherein the at least one optical sensor is engaged with a post-tensioned tendon anchor.

5. The monitoring system of claim 1, wherein the at least one optical sensor is a fiber Bragg grating strain gage.

6. The monitoring system of claim 1, wherein the test instrument is an optical interrogator.

7. The monitoring system of claim 1, wherein the monitoring system comprises a real-time monitoring system capable of calculating and displaying a feature of the post-tensioned tendon loading in real-time.

8. The monitoring system of claim 1, wherein the storage device is operative to receive and store the sensor measurement data for subsequent display, or for analysis, or for subsequent display and analysis.

9. The system of claim 1, wherein the processor is adapted to initiate an alarm when the post-tensioned tendon tensile loading is at or near a threshold level.

10. The monitoring system of claim 1, wherein the post-tensioned tendon is installed within a concrete structure and the sensor array is arranged in monitoring proximity to a shim of a post-tensioned tendon anchor.

11. The monitoring system of claim 1 further comprising a network interface in communication with the processor, wherein the network interface is adapted to provide remote access to the monitoring system.

12. A method for post-tensioned tendon monitoring comprising:
determining an expected value of post-tensioned tendon tensile loading;
receiving a signal from at least one optical sensor associated with a post-tensioned tendon assembly including receiving an optical strain gage wavelength representative of strain forces in an anchor portion of a post-tensioned tendon assembly, wherein said receiving a signal includes receiving a signal representative of temperature data associated with the monitored tendon;
analyzing the signal to determine a measured value of the post-tensioned tendon tensile loading wherein said analyzing the signal includes compensating the measured value of the post-tensioned tendon tensile loading with the temperature data;
optionally comparing the measured value with the expected value; and
generating a data output.

13. The method of claim 12, wherein
analyzing the signal to determine a measured value of post-tensioned tendon loading includes calculating an amount of tensile loading which exists within the post-tensioned tendon based on the anchor strain forces.

14. The method of claim 12 further comprising:
establishing a tolerance for the expected value of post-tensioned tendon tensile loading;
comparing the measured value of post-tensioned tendon tensile loading with the expected value of post-tensioned tendon tensile loading; and
optionally generating an alarm if the measured value is not within the established tolerance of the expected value.

15. The method of claim 12, wherein the optical strain gage sensor is a fiber Bragg grating strain gage.

16. The method of claim 12, wherein said generating a data output includes providing a data visualization representative of a feature of the post-tensioned tendon tensile loading.

17. The method of claim 16, including providing the data visualization in real-time.

18. The method of claim 12, including storing at least one of data associated with the optical sensor signal, the expected value of post-tensioned tendon tensile loading, and the measured value of post-tensioned tendon tensile loading; for later retrieval, or for visualization, or for analysis, or for later retrieval, visualization, and analysis.

* * * * *